United States Patent [19]

Brackenridge

[11] Patent Number: 4,774,368
[45] Date of Patent: Sep. 27, 1988

[54] PROCESS FOR MAKING META-ALKYL PHENOLS

[75] Inventor: David R. Brackenridge, Baton Rouge, La.

[73] Assignee: Ethyl Corporation, Richmond, Va.

[21] Appl. No.: 52,483

[22] Filed: May 21, 1987

[51] Int. Cl.$^4$ .............................................. C07C 37/02
[52] U.S. Cl. .................................... 568/796; 568/739
[58] Field of Search .................... 568/739, 770, 796

[56] References Cited

U.S. PATENT DOCUMENTS

| 2,523,707 | 9/1950 | Miller | 568/796 |
|---|---|---|---|
| 2,603,662 | 7/1952 | Stevens | 568/796 |
| 3,352,927 | 11/1967 | De Vriwa et al. | 568/796 |
| 4,001,340 | 1/1977 | Smith et al. | 568/770 |

OTHER PUBLICATIONS

Bottini et al, "J. Amer. Chem. Soc.", vol. 79, pp. 1458–1462, (1957).

*Primary Examiner*—Werren B. Lone
*Attorney, Agent, or Firm*—J. D. Odenweller

[57] ABSTRACT

A process for making meta-alkylphenols by reacting ortho-halo alkylbenzenes, e.g., ortho-chloro tert-butylbenzene, with an alkali metal base, e.g., potassium tert-butoxide.

9 Claims, No Drawings

PROCESS FOR MAKING META-ALKYL PHENOLS

BACKGROUND

Phenol is ortho-para directing such that the alkylation of phenol gives a mixture of ortho- and para-alkylphenols. In some applications a meta-alkylphenol is needed. For example, Eur. Pat. Appl. 173,993 (Chem. Abst. 105, 60432, 1986) describes the use of meta-tert-butylphenol as an intermediate for a rice herbicide.

One obstacle in the way of developing an efficient process for making meta-alkylphenols is that this isomer is almost impossible to separate from the para isomer by distillation as both have about the same boiling point. Accordingly a need exists for a process for making meta-alkyl phenols free of para-alkylphenols.

Bottini et al., J. Am. Chem. Soc. 79 1458 (1957) reported the reaction of ortho-chlorotoluene with sodium hydroxide to yield a mixture of ortho- and meta-cresol in approximately equal amounts.

SUMMARY

According to the present invention, a process is provided for making meta-alkylphenols by reacting an ortho-chloro or bromoalkylbenzene with a strong alkali metal base to obtain as the main product meta-alkyl phenols.

DESCRIPTION OF PREFERRED EMBODIMENTS

A preferred embodiment of the invention is a process for selectively making meta-alkylphenols from ortho-chloro- or bromo sec-alkyl or tert-alkylbenzene by reaction with a strong alkali metal base at elevated temperatures and recovering meta-alkyl phenols as the main product.

The process is applicable to a broad range of 2-halo alkyl benzenes. It is required that the 3-position be unoccupied except for hydrogen. The 4, 5 and 6 position may be unsubstituted or may be substituted with groups such as $C_{1-12}$ alkyl. Preferably both the 3 and 4 position are unsubstituted except for hydrogen. Some examples of the starting materials are 2-chloro isopropylbenzene, 2-chloro tert-butylbenzene, 2-bromo tert-pentylbenzene, 2-bromo 5-methyl tert-hexylbenzene, 2-(alpha-methylbenzyl)chlorobenzene, 2-(alpha,alphadimethylbenzyl)5-methyl chlorobenzene, 2-bromo cyclohexylbenzene, 2-chloro-5-methyl isobutylbenzene, 2-(1,1-dimethyldodecyl) bromobenzene, 2,4-di-tert-butyl chlorobenzene, 2-(1,1-dimethyltetradecyl)4-isopropyl chlorobenzene and the like.

Any strong alkali metal base can be used such as sodium hydroxide, potassium hydroxide, sodium isopropoxide, sodium tert-butoxide, potassium methoxide, potassium ethoxide, potassium isopropoxide, potassium tert-butoxide and the like.

As used herein "Conversion" means the mole percent of the initial 2-halo alkylbenzene that is reacted to form a different compound, not necessarily all the desired product. "Yield" is the mole percent of the converted starting material that forms any alkyl phenol, ortho or meta. "Selectivity" is the mole percent of the alkylphenol formed that is meta-alkyl phenol. For example, if 10 moles of 2-halo alkylbenzene are reacted with an alkali metal base and 2 moles of 2-halo alkylbenzene are left unchanged, then the conversion is 80%. If the reaction product contains 6 moles of alkylphenol then the yield is 75 percent. If 5 moles of the total alkylphenol are meta-alkyl phenol, then the selectivity is 83.33 percent.

If the desired selectivity is only moderate then an alkali metal hydroxide can be used in an aqueous solvent. Conversions of 75-85 percent and yields of 70-80 percent are generally achieved. Selectivity will range from about 75 percent with 2-halo sec-alkylbenzenes up to about 95 percent with 2-halo tert-alkylbenzenes. If more selectivity is needed, the preferred bases are the alkali metal alkoxides in an alcohol solvent. Using potassium tert-butoxide in tert-butanol, conversions of about 100 percent with yields of 70-80 percent and selectivity ranging from about 92 percent with 2 halo sec-alkyl benzenes up to 99 percent with 2-halo tert alkyl benzenes can be achieved.

The reaction is conducted by mixing the alkali metal base with the 2-halo alkylbenzene. With alkali metal hydroxides, an aqueous solvent is used. A phase transfer agent such as a quaternary ammonium halide is not needed but may improve results.

With alkali metal alkoxides, an alcohol solvent is preferred. The preferred alcohol corresponds to the alkoxide group. Potassium tert-butoxide in tert-butanol is the most preferred solvolysis system.

The amount of solvent can range from about 10 percent up to 300 percent or more based on the weight of the 2-halo alkyl benzene. The amount of base should be at least equivalent to the 2-halo alkylbenzene and preferably in excess. A preferred range is about 2–10 moles of base per mole of 2-halo alkylbenzene and more preferably about 3–5 moles of base per mole of 2-halo alkyl benzene.

The reaction is conducted at an elevated temperature. The temperature should be high enough to cause the reaction to proceed but not so high as to degrade the products. A useful range is about 100°–350° C. A more preferred temperature range is about 200°–300° C. and a most preferred temperature range is about 230°–275° C.

The reaction temperature is generally above the boiling point of the solvent so the reaction is preferably conducted in a closed autoclave at whatever pressure is attained due to the vapor pressure of the reaction mixture. This is referred to as autogenous pressure.

Workup of product is conventional. In an aqueous system the reaction mixture can be neutralized and extracted with a solvent, e.g., ether, to recover the alkali phenols and byproducts, e.g., diphenyl ethers, and unreacted starting material. These can be separated by distillation.

When an alcohol solvent is used the solvent can be distilled out under vacuum and the residue acidified and extracted with a solvent, e.g., ether. The extract can be dried over a desiccant such as magnesium sulfate and distilled to recover the desired meta-alkylphenol.

The following examples show how the reaction is conducted.

EXAMPLE I

In a pressure reaction vessel was placed 10.0 g (0.059 mole) 2-chloro-tert-butylbenzene and 39.1 g (0.59 mole) 85% KOH dissolved in 150 ml water. The vessel was sealed and while stirring heated to 340° C. and held 4 hours. It was then cooled and vented. The mixture was extracted with ether to recover 5.13 g oil. The aqueous phase was acidified and extracted with ether to recover 4.04 g oil. Analysis of both fractions by NMR, GC/MS and capillary GC showed a 77.2% conversion and 74.1% yield of tert-butylphenols. Selectivity to meta-isomer was 98.4%. A trace of phenol was detected.

EXAMPLE 2

This run was conducted the same as Example 1 except using a 22 hour reaction period. The ether extract of the basic solution gave 5.16 g oil and the ether extract of the acid solution gave 4.78 g oil. Analysis gave 84.8% conversion and 72.2% yield of tert-butylphenols. Selectivity of meta-isomer was 98.4%.

EXAMPLE 3

In a pressure vessel as used in Example 1 was placed 10.0 g o-chloro isopropylbenzene, 42.5 g 85% KOH and 160 ml $H_2O$. The mixture was stirred 4 hours at 334° C. Work-up as in Example 1 gave 5.45 g basic extract and 3.85 g acidic extract. Analysis of both gave a 62% conversion and 80.0% yield of isopropylphenols with a selectivity of 70.7% to meta-isopropylphenol.

EXAMPLE 4

This run was conducted the same as Example 3 except that a 23-hour reaction period was used. Work-up as in Example 1 gave 5.12 g basic extract and 3.52 g acidic extract. Analysis gave a 76.1% conversion and a 72.0% yield of isopropylphenols with a meta selectivity of 78.8%.

EXAMPLE 5

In an autoclave was placed 10.0 g 2-chloro tert-butyl benzene and 26.5 g potassium tert-butoxide in 100 ml tert-butanol. The clave was sealed and stirred 4 hours at 240° C. The cooled mixture was extracted with ether and the ether extract water washed to remove tert-butanol. The extract was dried over $MgSO_4$, filtered and the ether distilled out to leave 6.8 g of residual oil.

The aqueous reaction mixture was acidified and again extracted with ether. The extract was water-washed and dried over $MgSO_4$. Ether was distilled out leaving 3.54 g residual oil. Analysis of both oils gave a 100% conversion and a 67.2% yield of tert-butyl phenols. The selectivity to meta-isomer was 99.2%. The main by-product wa di-(tert-butylphenyl) ether.

EXAMPLE 6

An autoclave was charged with 10.0 g 2-chloro isopropylbenzene, 41.0 g potassium tert-butoxide in 150 ml tert-butanol. The clave was sealed and stirred at 240° C. for 4 hours. Work-up as in Example 5 gave 5.3 g of basic extract and 5.3 g of acidic extract. Analysis of both extracts showed 99.7% conversion and 82.1% yield of isopropylphenols of which 92.5% was meta-isomer.

EXAMPLE 7

An autoclave was charged with 20.1 g 2-chlorotoluene and 62.6 g potassium tert-butoxide in 175 ml tert-butanol. The reaction was conducted as in Example 5 to give 4.5 g basic extract and 12.51 g of acidic extract. Analysis of both extracts showed 100% conversion and 66.2% yield of cresols of which 62.5% was meta-isomer.

These results show that the process is very selective to the meta-alkylphenol isomer especially when the alkyl is sec or tert and the base is an alkali metal sec or tert-alkoxide.

I claim:
1. A process for making a meta-alkylphenol in high yield and selectivity, said process comprising reacting an ortho-halo-alkylbenzene with an alkali metal base at an elevated temperature high enough to cause the reaction to proceed but not so high as to degrade the products wherein said alkyl is a sec- or tert-alkyl and said halo is chlorine or bromine.
2. A process of claim 1 wherein said alkyl is a tert-alkyl.
3. A process of claim 1 wherein said base is an alkali metal alkoxide.
4. A process of claim 3 wherein said alkali metal alkoxide is an alkali metal tert-alkoxide.
5. A process of claim 4 wherein said alkyl is a tert-alkyl containing 4–8 carbon atoms.
6. A process for making meta-tert-butylphenol, said process comprising reacting ortho-halo tert-butylbenzene with sodium or potassium tert-butoxide at an elevated temperature in the range of 100°–350° C. and recovering meta-tert-butylphenol as the main product.
7. A process of claim 6 wherein said halo is selected from chloro or bromo.
8. A process of claim 7 wherein said halo is chloro.
9. A process of claim 8 wherein said temperature is in the range of 200°–300° C.

* * * * *